US00RE34698E

United States Patent [19]

Miyazaki et al.

[11] E Patent Number: Re. 34,698

[45] Reissued Date of Patent: Aug. 16, 1994

[54] METHOD OF PRODUCING SALINOMYCIN ANTIBIOTICS

[75] Inventors: Yukio Miyazaki, Ageo; Akira Shibata, Zama; Tateo Yahagi, Kawagoe; Masayuki Hara; Kaoru Hara, both of Tokyo; Singo Yoneda, Kuki; Hiroko Kasahara, Matsudo; Yuko Nakamura, Tokyo, all of Japan

[73] Assignee: Kaken Chemical Company, Limited, Tokyo, Japan

[21] Appl. No.: 10,786

[22] Filed: Jan. 29, 1993

Related U.S. Patent Documents

Reissue of:

[64] Patent No.: 4,212,942
Issued: Jul. 15, 1980
Appl. No.: 911,231
Filed: May 31, 1978

[30] Foreign Application Priority Data

May 31, 1977 [JP] Japan ..... 52-62802
Jun. 1, 1977 [JP] Japan ..... 52-63215

[51] Int. Cl.[5] ..... C12P 17/18; C12N 1/38; C12N 1/20

[52] U.S. Cl. ..... 435/119; 435/244; 435/253.5

[58] Field of Search ..... 435/119, 244, 253.5; 195/80 R, 114

[56] References Cited

U.S. PATENT DOCUMENTS 4,035,481 7/1978 Berg et al. ..... 424/122
4,212,942 7/1980 Miyazaki et al. ..... 435/119

FOREIGN PATENT DOCUMENTS 1378414 12/1974 United Kingdom .

OTHER PUBLICATIONS

W. M. Stark, Monensis, A Biologically Active Compound, Fermentation Advances, Academic Press, 1969, pp. 517–540.

*Primary Examiner*—Douglas W. Robinson
*Assistant Examiner*—Jeffrey J. Sevigny
*Attorney, Agent, or Firm*—Oblon, Spivak, McClelland, Maier & Neustadt

[57] ABSTRACT

Polyether type antibiotics are produced by culturing a polyether type antibiotic-producing microorganism is a medium containing a fatty acid or its precursor and ammonia or an ammonium salt or urea.

4 Claims, No Drawings

METHOD OF PRODUCING SALINOMYCIN ANTIBIOTICS

Matter enclosed in heavy brackets [ ] appears in the original patent but forms no part of this reissue specification; matter printed in italics indicates the additions made by reissue.

BACKGROUND OF THE INVENTION

The present invention relates to an improvement in a method of producing polyether type antibiotics in an industrial scale.

As polyether type antibiotic there have been known Monensin (Journal of American Chemical Society, Vo. 89, page 5757, 1967), X-206 (Chemical Communications, 927, 1971), Salinomycin (British Pat. No. 1,378,414), SY-1 substance (Japanese O.P.I. No. 86191/76), SY-2 substance (Japanese Patent Application No. 5762/77), 4-methylsalinomycin (A 28086 substance) (Japanese O.P.I. No. 9788/76), Lasalocid (Journal of American Chemical Society, Vol. 73, 5295, 1951), Dianemycin (Journal of Antibiotics, Vol. 22, page 161, 1969), Nigericin (Biochemical and Biophysical Research Communication, Vol. 33, page 29, 1968), A-204 A (Journal of American Chemical Society, Vol. 95, 3399, 1973) and the like, and among these, Salinomycin, 4-methylsalinomycin, SY-1, SY-2, SY-3, SY-4, SY-5, SY-6, SY-7 and SY-8 substance are called Salinomycin type antibiotics because they have the similar chemical structures.

In this invention, the term "salinomycins" means each compound, or any mixture of at least two compounds, selected from the group consisting of salinomycin, SY-1, SY-2, SY-3, SY-4, SY-5, SY-6 and the like.

The present inventors already found that salinomycin, SY-1 and SY-2 were produced in the culture of Streptomyces albus waxman and henrich No. 80614 strain (FERM-P. No. 419), and succeeded in isolating the antibiotics from the culture (British Pat. No. 1378414, Japanese Unexamined Patent Publication No. 86191/1976 and Japanese Patent Application No. 5762/1977).

The inventors continued the study and found that, when the above strain is cultured in the medium containing fatty acid or its precursor, it produces salinomycin, SY-1, and SY-2 in high yield, and also produces new compounds such as SY-3, SY-4, SY-5, SY-6, SY-7 and SY-8.

As described in said literatures, these are produced by culturing each antibiotic producing microorganism belonging to the genus of Streptomyces. However, the yield of each antibiotic produced by such known method is not always satisfactory.

SUMMARY OF THE INVENTION

It is an object of the present invention to provide a method of producing polyether type antibiotics in remarkably high yields with industrial advantages.

Another object of the present invention is to provide a method of producing Salinomycin type antibiotics such as salinomycin, 4-methylsalinomycin, SY-1, SY-2, SY-3, SY-4, SY-5, SY-6, SY-7 and SY-8 substances in high yield.

The foregoing and other objects of the present invention have been attained by culturing a polyether type antibiotic-producing microorganism in a medium containing a fatty acid or its precursor and ammonia or an ammonium salt or urea.

DETAILED DESCRIPTION OF THE PREFERRED EMBODIMENTS

In the special feature of the present invention, salinomycin type antibiotics such as salinomycin, 4-methylsalinomycin, SY-1, SY-2, SY-3, SY-4, SY-5, SY-6, SY-7 and SY-8 substances are produced by culturing a salinomycin type antibiotic-producing microorganism in a medium containing a fatty acid or its precursor and ammonia or an ammonium salt or urea.

The fatty acids used in the present invention are saturated or unsaturated fatty acids, for example, acetic acid, propionic acid, caproic acid, capric acid, palmitic acid, stearic acid, methacrylic acid, undecylic acid, and particularly linolic acid, linolenic acid or oleic acid being preferable. The precursor of fatty acid means a substance that is capable of giving said fatty acid outside or inside the microorganism cell, such as mono-di- or triglycerides of fatty acid, esters of fatty acid or salts of fatty acid. Further, there can be used soy bean oil, safflower oil, cotton seed oil, sesame oil, olive oil, rape oil, peanut oil, maize oil (corn oil), sunflower oil and like vegetable oils, code oil and like fish oils and lard and like animal fat-and-oils, which contain said precursors.

The esters of fatty acid can be $C_1$–$C_{18}$ alcohols of said fatty acid.

The salts of fatty acid can be ammonium salt and alkali metal salts and alkaline earth metal salts of said fatty acid.

The addition amount is generally about 1–25%, particularly about 12–20% based on the medium.

Ammonia is used in gaseous form or in the form of aqueous solution. As ammonium salt there are used ammonium salts of inorganic acids such as hydrochloric acid, sulfuric acid, nitric acid and phosphoric acid or organic acids such as acetic acid, propionic acid, higher fatty acid, oxalic acid, tartaric acid, hydrogentartaric acid, citric acid, lactic acid and malic acid. The addition amount is generally about 0.1–1.0% particularly about 0.3–0.5% based on the medium.

As for the time for addition of these additives, addition is effective so long as production of potency of polyether type antibiotic continues, and is conducted at any time either before or after beginning of cultivation. Although the cultivation conditions of the present invention can be selected in accordance with the methods described in said known literatures, excepting that fatty acid or its precursor is used as major carbon source and that ammonia or ammonium salt is used as essential component of the medium, it is possible to raise the production efficiency by varying the conditions depending on the kind of antibiotics.

The microorganism used in the present invention include generally polyether type antibiotics producing strains belonging to the genus of Streptomyces as well as the strains described in said literatures and their natural or artificial mutants.

Separation and purification of the products can be carried out in accordance with known methods. Since the objective substance is often contained mainly in the solid portion containing the cells when the production amount of the objective substance is abundant, it is desirable to vary the extraction step properly in order to heighten the recovery percentage of the objective-substance from the solid portion. It is possible to use the objective compound in the state that it is contained in the solid portion depending on the use purposes, without separating the objective substance from the solid portion.

According to the present invention the production amount of polyether type antibiotics, particularly Salinomycin type antibiotics can be remarkably increased. For example, the yield of Salinomycin is generally 100–300 γ/ml in known method, whereas the yield is about 10,000–20,000 γ/ml in the medium containing fatty acid or its precursor, and the yield is further increased to about 50,000–80,000 γ/ml when said medium is further added by ammonia or ammonium salt.

The preferable feature of the present invention to produce salinomycin type antibiotics will be further illustrated.

According to the method of this invention, salinomycins mainly occur in the mycerial mass, at it is preferable to recover salinomycins from the mycelial mass. In addition to salinomycin, SY-1, and SY-2, another new compounds, especially SY-3, SY-4, SY-5, SY-6, and the like are obtained from the culture.

The strains used in this invention include Streptomyces albus No. 80614 and its mutants artificially or naturally produced, as well as the other Streptomyces strains capable of producing salinomycins. However, some of the salinomycins can occasionally not be detected in the salinomycin and SY-1 can be applied to the isolation of salinomycins, however, as for salinomycin, because a large portion of salinomycin is contained in mycelial mass, the extraction process is preferably modified so as to increase the recovery rate of salinomycin. For example, it is preferred to adjust the whole fermentation broth to pH 2.0–6.0 to precipitate salinomycin, and then to extract the mycerial mass together with the precipitate thus formed with an organic solvent. Among the preferred solvents are acetone, ethyl acetate, butyl acetate, n-hexane, chloroform and the like. After applying the solution to the absorptive materials suitable for the absorption of salinomycins, the salinomycins are eluted by a suitable solvent system.

the effluent is collected in 2–5 fractions according to the purpose. Separation and purification of salinomycins are effected by the procedures utilizing the difference between the properties of desired compound and impurities. Namely, chromatography, solvent extraction and the like are repeated for each fraction to give salinomycin, SY-1, SY-2, SY-3, SY-4, SY-5, SY-6, SY-7, SY-8, and the like, individually or as mixtures. The resulting products can be further purified by recrystallization or chromatography.

The properties of salinomycins obtained by the process of this invention are shown in the following table.

According to the preferred feature of this invention

| | Characteristics of salinomycins Characteristics | | | | | | | |
|---|---|---|---|---|---|---|---|---|
| | Rf values*** Solvent system | | | | | | | |
| Factor | $CHCl_3$2O MeOH 1 | EtOAc 4 $(CH_3)_2CO$ 1 | EtOAc | 10% $H_2SO^*_4$ | Vanillin** reagent | $m^{+\cdot}$ m/e (methyl ester) | antimicrobial activity*** 100 γ/ml | Remarks |
| SY-1 | 0.50 | 0.95 | 0.83 | Yellow | | 748 | 21 | |
| Salinomycin | 0.40 | 0.90 | 0.60 | | Red | 764 | 30 | |
| SY-2 | 0.35 | 0.35 | 0.15 | Yellow | 748 | 20 | | |
| SY-3 | 0.45 | 0.92 | 0.78 | Yellow | | 748 | 28 | (SY-1 analogue) |
| SY-4 | 0.26 | 0.30 | 0.13 | | Red | 764 | 25 | (Salinomycin analogue) |
| SY-5 | 0.17 | 0.19 | 0.10 | | Red | 766 | 20 | (18, 19-dihydrosalinomycin analogue) |
| SY-6 | 0.05 | 0.06 | 0.03 | | Red | 782 | 15 | (18, 19-dihydrosalinomycin analogue) |
| SY-7 | 0.80 | 0.98 | 0.95 | Yellow | | | 17 | (SY-1 analogue) |
| SY-8 | 0.11 | 0.13 | 0.06 | Yellow | | | 14 | (SY-1 analogue) |
| SY-1: | 20-deoxy-salinomycin | | | | | | | |
| SY-2: | stereoisomer of SY-1 | | | | | | | |
| SY-4: | 5-hydroxy-salinomycin | | | | | | | |
| SY-5: | 18, 19-dihydro-salinomycin | | | | | | | |
| SY-8: | stereoisomer of SY-5 | | | | | | | |

*Spray on silica gel plate (room temperature)
**Dissolve 3 g of vanillin in 100 ml methanol. Add 0.5 ml of $H_2SO_4$ with stirring. Spray on silica gel plate. Heat for 5 min at 60° C.
***Silica gel TLC (Wakogel B-10, thickness 0.25 mm)
****diameter of inhibitory zone test organism: *Batilus subtilis* culture, depending on the strain and fermentation conditions.

Fermentation conditions employed in this invention can be any one commonly used for culturing Actinomycetes, except that main carbon source should be a fatty acid or its precursor. Maximum production of salinomycins usually occurs after 150 to 260 hours from the start of fermentation. Ratio of each of salinomycins produced sometimes varies depending on the incubation time. Naturally, the composition of medium and fermentation conditions should be decided for each strain and external conditions, so that most desirable results are obtained.

Salinomycins can be isolated from the culture medium by utilizing the physico-chemical properties of salinomycins. Because salinomycins are structurally related to each other, the known extraction methods for salinomycin, SY-1, and SY-2, especially salinomycin are obtained in surprisingly higher yield than the known process. New compounds, SY-3 through -8 are also obtained according to this invention. They are comparable to salinomycin in their activities against microorganisms and useful as medicines. Also, because of their structural similarity to salinomycin, their usefulness as veterinary medicines looks very likely.

REFERENCE EXAMPLE 1

Streptomyces albus waxman and henrich No. 80614 strain (FERM-P. No. 419) is inoculated to a medium containing glycerine 2.0%, peptone 0.5% and meat extract 0.5% and cultured at 33° C. for 48 hours under shaking. 1 liter of this culture liquid is inoculated to 100 liters of liquid medium (200 liter tank made of stainless steel) containing glucose 2%, starch 1%, soy bean powder 2.5%, beer yeast 0.4%, meat extract 0.1%, sodium chloride 0.2% and antifoaming agent KM-68-2F (product of Shinetsu Chemical Industry Co., Ltd., silicone type) 0.1% and cultured at 33° C. for 144 hours under stirring with the aeration volume of 100 l/m. There is obtained a culture liquid containing 100–300 γ/ml of Salinomycin.

REFERENCE EXAMPLE 2

The 80614 strain which is the same strain as described in Example 1 is inoculated to a medium containing glycerine 2.0%, peptone 0.25%, meat extract 0.5% and edible salt 0.1%, and cultured at 33° C. for 48 hours under shaking.

This culture liquid is an amount corresponding to 1% of the medium is inoculated to the medium containing glucose 4.0%, soy bean powder 1.0%, beer yeast 1.0% and calcium carbonate 0.2%, and cultured for 30 hours at 33° C. under shaking, and this culture liquid is made the second-stage pre-culture liquid. One liter of this second-state preculture liquid is inoculated to 100 liters of liquid medium containing soy bean oil 10%, glucose 1.0%, soy bean powder 1.0%, calcium carbonate 0.5%, potassium secondary phosphate 0.01%, and cultured for 210 hours at 33° C. with an aeration volume of 100 l/m under stirring. There is obtained a culture liquid containing 20,000 γ/ml of Salinomycin.

EXAMPLE 1

(A) Production of salinomycin

The 80614 strain which is the same strain as described in Example 1 is inoculated to a medium containing glycerine 2.0%, peptone 0.25%, meat extract 0.5% and edible salt 0.1%, and cultured at 33° C. for 48 hours under shaking. This culture liquid in an amount corresponding to 1% of the medium is inoculated to the medium containing glucose 4.0%, soy bean powder 1.0%, beer yeast 1.0% and calcium carbonate 0.2%, and cultured for 30 hours at 33° C. under shaking, and this culture liquid is made the second-stage, pre-culture liquid. One liter of this second-stage pre-culture liquid is inoculated to 100 liters of liquid medium containing soy bean oil 10%, glucose 1.0%, soy bean powder 1.0%, calcium carbonate 0.5%, potassium secondary phosphate 0.01%, and cultured for 210 hours at 33° C. with an aeration volume of 100 l/m under stirring. There is obtained a culture liquid containing 20,000 γ/ml of salinomycin (salinomycin only).

(B) Separation and purification of salinomycin, SY-1 and SY-2.

The culture liquid obtained in (A) is adjusted to pH 4.5–5.0 with dilute hydrochloride, admixed with 4% by weight per volume of filter aid with stirring, and filtered. The filtrate (80 liters) is extracted with 50 liters of butyl acetate with stirring. Mycelial mass is extracted with 30 liters of butyl acetate. Both butyl acetate solutions are combined and washed with 20 liters of 5% aqueous sodium bicarbonate solution. One liter of the washed butyl acetate solution is concentrated under vacuum to dryness to give 250 g of crude powder of salinomycin containing trace amount of SY-1 and SY-2.

Fifty grams of the crude salinomycin powder is dissolved in ethyl acetate and applied to column (50 g of active almina, commercial product of Wako Junyaku Co.). After washing the column with one liter of ethyl acetate, salinomycin and SY-1 are eluted with a 100:5 mixture of ethyl acetate-methanol solution. The fractions containing salinomycin and SY-1 are combined and concentrated. The concentrate is diluted in 50 ml of chloroform-methand solution (100:2) and applied to the column of 300 g silica gel (Wakogel-200, Wako Junyaku Co.) packed in the same solvent mixture. Elution is carried out with the same solvent mixture to give pure salinomycin fraction and pure SY-1 fraction. Each fraction is concentrated and crystallized from acetone-water solution to give 5 g of salinomycin and 30 mg of SY-1 in pure crystals, respectively.

The almina column as mentioned above is further developed with a 100:15 mixture of ethyl acetate-methanol to elute SY-2, which is separated and purified by silica gel chromatography in the same manner as described above, and crystallized from acetone-water solution to give 3 mg of pure crystalline SY-2.

EXAMPLE 2

(A) Salinomycin is cultured in the same manner as described in Example 1.

(B) Recovery of salinomycins

The culture obtained in (A) is adjusted to pH 4.5–5.0, heated at 60° C. for 10 minutes with stirring, admixed with 4% by weight per volume of filter aid with stirring and filtered. The resulting mycelial mass contains salinomycins and SY group compounds in high yield.

(C) Separation of salinomycins complex

Mycelial mass obtained in (B) is extracted twice with 50 liters of ethyl acetate. The extracts are combined and washed with 50 liters of 5% aqueous sodium bicarbonate solution. Ethyl acetate phase is concentrated under vacuum to dryness to yield 7 kg of crude salinomycins complex containing SY group compounds.

(D) Separation and purification salinomycin

Seven kg of crude powder obtained in (C) is dissolved in 100 liters of hexane, concentrated under vacuum to 20 liters and left at 5° C. to give 2.7 kg of crude crystallin salinomycin. After repeating this procedure, recrystallization of salinomycin from hexane gives 2.4 kg of pure salinomycin sodium salt.

(E) Separation and purification of SY group compounds

The mother liquor separated from the precipitate in the process in (A) is concentrated to dryness to give 4.6 kg of complex containing a small amount of salinomycin and SY group compounds. The complex is dissolved in 50 liters of hexane-ethyl acetate solvent mixture (2:1) and applied to the column of 12 kg of almina packed in the same solvent system, developed with 20 liters of a 100:2 mixture of ethyl acetate-methanol to elute SY-3, SY-7 and salinomycin. Two hundred g of the mixture of salinomycin and SY-1 is separated by precipitation in the same manner as described in (D). The filtrate containing SY-3 and SY-7 is concentrated to dryness to give 100 g of crude powder.

One hundred g of crude powder thus obtained is dissolved in 300 ml of a 100:2 mixture of chloroform-methanol and applied to the column of 6 kg of silica gel (Wakogel C-200, Wako Junyaku Co.), and developed with the same solvent mixture. Each of SY-3 and SY-7 fractions is concentrated and applied to silica gel thin layer chromatogram (Wakogel B-10 with thickness of 0.25 mm, solvent system; a 20:1 mixture of chloroform-methanol). SY-3 and SY-7 are collected by scraping off the areas with Rf values 0.45 and 0.80, respectively. The silica gel holding each compound is eluted with a 20:1 mixture of chloroform-methanol and the solvent mixture is removed by evaporation to give 18 mg of SY-3 and 35 mg of SY-7 both in pure powders.

The above almina column is eluted with 20 liters of a 5:1 mixture of ethyl acetate-methanol, and the effluent is concentrated under vacuum to give 200 g of crude powder, which contains the complex of SY-2, SY-4, SY-5, SY-6 and SY-8. These compounds are isolated individually by silica gel column chromatography. Two hundred g of the crude powder is dissolved in 500 ml of a 100:2 mixture of chloroform-methanol, applied to the column of 2 kg silica gel (Wakogel C-200) packed in the same solvent mixture, and developed with the same solvent mixture to give each fraction containing SY-2, SY-4, SY-5, SY-6 and SY-8, respectively. Each fraction is concentrated to dryness to give 20 g of SY-2, 300 mg of SY-4, 250 mg of SY-5, 800 mg of SY-6 and 100 mg of SY-8 as crude powders, respectively. Crude SY-2 powders are crystallized from acetone water to give 15 g of pure crystalline SY-2.

Other crude powders are purified by thin layer chromatography of silica gel in the same manner as employed in the separation and purification of SY-3 and SY-7 to give 26 mg of SY-4, 20 mg of SY-5, 80 mg of SY-6 and 30 mg of SY-8 each in pure powders.

EXAMPLE 3

(A) The second-stage pre-culture liquid of Example 1 in an amount corresponding 10% of the medium is inoculated to the medium containing glucose 4%, soy bean powder 3%, defatted wheat germs 3.0%, calcium carbonate 0.2% and antifoaming agent KM-68-2F 0.1%, and cultured for 24 hours at 33° C. to give the third-stage pre-culture liquid.

Ten liters of the third-stage pre-culture liquid is inoculated to the medium containing soy bean oil 16%, soy bean powder 0.5%, defatted wheat germs 1.0%, sodium chloride 0.2%, potassium chloride 0.2%, ammonium sulfate 0.3%, calcium secondary phosphate 0.02%, magnesium sulfate 0.01% and antifoaming agent KM-68-2F 0.1%, and cultured for 290 hours at 33° C. with an aeration volume of 100 l/m under stirring. The production amount of salinomycin at the end of cultivation is 60,000 γ/ml (salinomycin only). In this case the similar production amount is attained even when soy bean oil is added in a small amount at the beginning and then the addition amount is increased. No difference in production amount is observed between cases in which silicone type and polyether type antifoaming agents are used.

(B) Treat the fermentation broth obtained in (A) according to the procedure of Example 2 (B) to give mycelial mass containing salinomycins in high yield.

(C) Treat the mycelial mass obtained in (B) according to the procedure of Example 2 (C) to give 16 kg of the complex of SY-1, 2, 3, 4, 5, 6, 7 and 8.

(D) Dissolve 16 kg of crude powder obtained in (C) in 100 liters of hexane and concentrate under vacuum to 40 liters. Then treat the solution according to the same procedure described in Example 2 (D) to give 7.1 kg of crude crystallin salinomycin and then 6.3 kg of pure salinomycin sodium salt.

(E) The mother liquor separated from crystals in the process in (D) is concentrated to dryness to give 9.7 kg of the complex containing SY-1 through -8. The complex is dissolved in 100 liters of a 2:1 mixture of hexane-ethyl acetate, applied to the column of 20 kg of almina in the same manner as described in Example 2 (E) and developed with 30 liters of a 100:2 mixture of ethyl acetate-methanol to elute SY-1, SY-3 and SY-7. The effluent is treated in the same manner as described in Example 2 (E) to give 400 g of salinomycin-SY-1 mixture and 130 g of crude powder containing SY-3 and SY-7.

One hundred and thirty g of said crude powder is dissolved in 400 ml of chloroform-methanol solution (100:2), treated by silica gel column chromatography (8 kg of silica gel is used) to give SY-3-and SY-7-fractions. Each fraction is chromatographed over silica gel thin layer according to Example 2 (E), and after removing the solvent by evaporation, 30 mg of SY-3 and 50 mg of SY-7 are obtained as pure powders.

The above almina column is eluted with 40 liters of a 5:1 mixture of ethyl acetate-methanol and the effluent is concentrated to dryness to give 250 g of crude powder containing the complex of SY-2, SY-4, SY-5, SY-6 and SY-7. The complex is dissolved in 600 ml of chloroform-methanol solution (100:2), and then treated by chromatography (20 kg silica gel) in the same manner as described above to give 40 g of SY-2, 600 mg each of SY-4 and SY-5, 1900 mg of SY-6 and 300 mg of SY-8 as crude powders, purification of which according to the procedure of Example 2 (E) gives 30 g of crystallin SY-3, 180 mg of SY-4 powder, 120 mg of SY-5 powder, 350 mg of SY-6 powder and 90 mg of SY-8 powder, all in pure form.

EXAMPLE 4

The third-stage pre-culture liquid in Example 3 in an amount corresponding to 10% of the medium is inoculated to the medium (50 ml) containing each fat-and-oil shown in the following Table 12%, soy bean powder 0.5%, defatted wheat germs 1.0%, sodium chloride 0.2%, potassium chloride 0.2%, calcium carbonate 0.5%, ammonium soifate 0.3%, potassium secondary phosphate 0.02% and magnesium sulfate 0.01%, and cultured at 33° C. for 216 hours under shaking. The production amounts of salinomycin at the end of cultivation are shown in the following Table.

| Fat-and-oil | Yield of salinomycin (γ/ml) |
|---|---|
| soy bean oil | 38000 |
| purified soy bean oil (Shirashime oil) | 36000 |
| Sesame oil | 36000 |
| rape oil | 35000 |
| safflower oil | 39000 |
| olive oil | 37000 |
| cod oil | 37000 |
| methyl oleate | 34000 |
| methyl myristate | 38000 |
| methyl linolate | 38000 |

From the resulting culture, salinomycins are separated individually and purified according to the procedures of Examples 1–3.

What is claimed is:

1. A method of producing salinomycins, which comprises culturing a salinomycins-producing Streptomyces microorganism in a medium containing *12–25%* fatty acid or its precursor and ammonia or an ammonium salt and recovering the salinomycins from the culture.

2. The method of claim 1 wherein salinomycin is recovered together with the mycelial mass from the culture.

3. The method of claim 1 or 2 wherein SY-1, SY-2, SY-3, SY-4, SY-5, and/or SY-6 is recovered from the culture.

4. The method of claim 1, wherein salinomycin, 4-methylsalinomycin, SY-1, SY-2, SY-3, SY-4, SY-5, SY-6, SY-7 and/or SY-8 is recovered from the culture.

* * * * *